Figure 1:
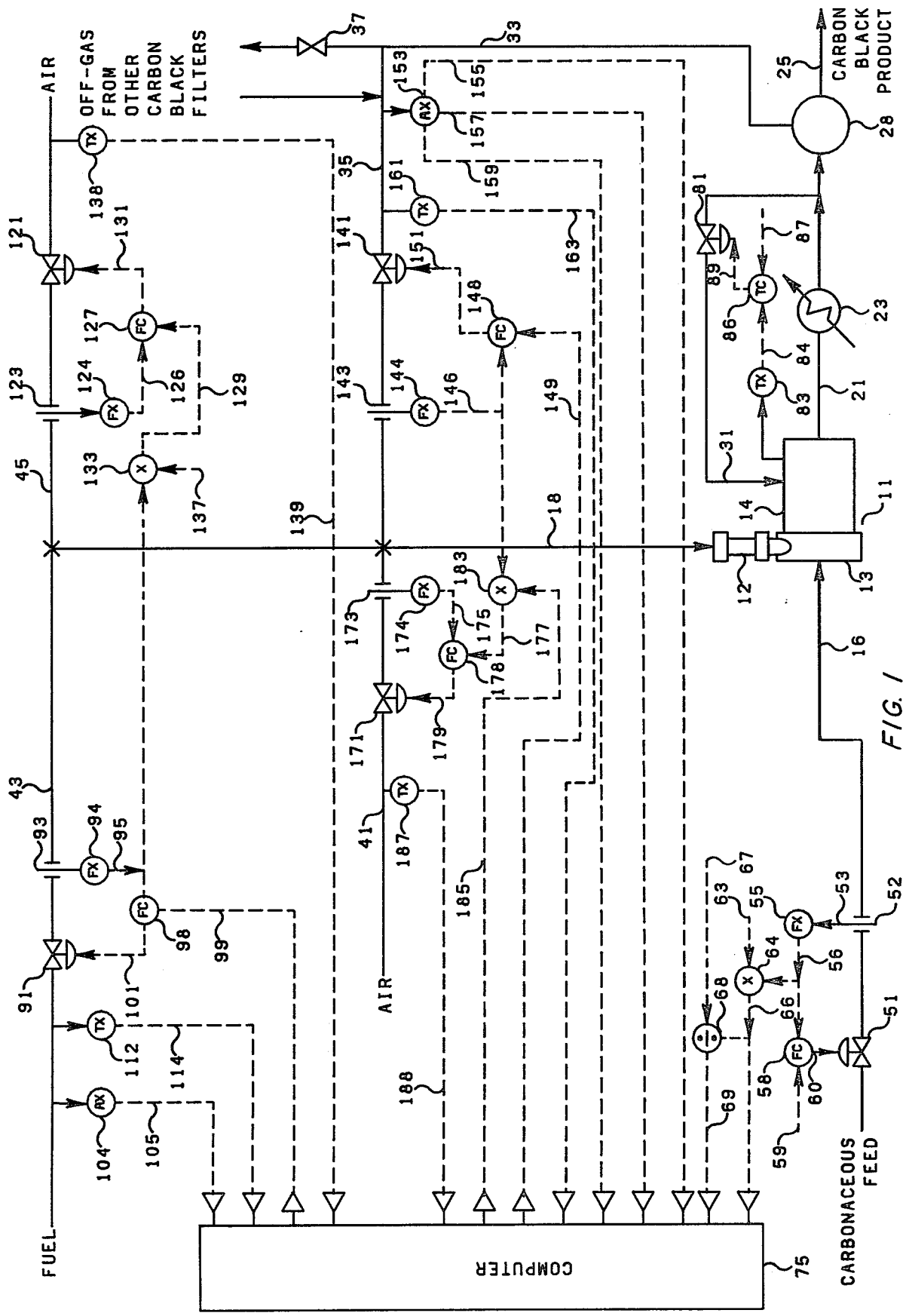

United States Patent [19]

Lewis

[11] 4,237,092
[45] Dec. 2, 1980

[54] METHOD AND APPARATUS FOR PRODUCING CARBON BLACK

[75] Inventor: Robert J. Lewis, Bartlesville, Okla.

[73] Assignee: Phillips Petroleum Company, Bartlesville, Okla.

[21] Appl. No.: 946,654

[22] Filed: Oct. 2, 1978

[51] Int. Cl.$^3$ .................... C09C 1/48; G01N 31/00
[52] U.S. Cl. .................... 422/62; 364/500; 422/111; 422/150; 423/450
[58] Field of Search ........... 422/150, 151, 62, 119, 422/156, 105, 111; 423/450, 455, 456, 457, 458; 364/500, 503

[56] References Cited

U.S. PATENT DOCUMENTS

| | | | |
|---|---|---|---|
| 2,781,246 | 2/1957 | Goldtrap | 423/450 |
| 3,005,688 | 10/1961 | Williams | 422/62 |
| 3,169,047 | 2/1965 | Osburn, Jr. | 423/450 |
| 3,350,173 | 10/1967 | Colby, Jr. et al. | 422/150 X |
| 3,369,870 | 2/1968 | Ganz et al. | 422/150 X |
| 3,390,960 | 7/1968 | Forseth | 422/150 X |
| 3,438,732 | 4/1969 | Morel | 422/150 X |
| 3,592,599 | 7/1971 | Gohlke et al. | 423/450 |
| 3,645,685 | 2/1972 | Crouch | 422/150 X |
| 3,722,811 | 3/1973 | Osburn | 236/14 |
| 3,993,447 | 11/1976 | Buss et al. | 423/450 |
| 3,998,934 | 12/1976 | Vanderveen | 423/456 X |
| 4,080,434 | 3/1978 | Buss et al. | 422/150 X |
| 4,115,862 | 9/1978 | Stewart | 364/500 |

FOREIGN PATENT DOCUMENTS

| | | | |
|---|---|---|---|
| 531394 | 10/1956 | Canada | 423/458 |
| 1130100 | 5/1962 | Fed. Rep. of Germany | 423/456 |

*Primary Examiner*—Frank W. Lutter
*Assistant Examiner*—Roger F. Phillips

[57] ABSTRACT

In a carbon black manufacturing process a method and apparatus is provided whereby the off-gas from at least one carbon black manufacturing process is utilized both to lower the temperature of the hot combustion gases and to provide some heat to the hot combustion gases by being burned in the combustion tunnel of a carbon black reactor. A portion of the off-gas is utilized while still holding the total volume of the hot combustion gases substantially constant at a preselected substantially constant temperature to insure a substantially constant quality of carbon black.

12 Claims, 2 Drawing Figures

METHOD AND APPARATUS FOR PRODUCING CARBON BLACK

This invention relates to carbon black production. In a specific aspect this invention relates to method and apparatus for using off-gas from at least one carbon black manufacturing process to lower the temperature of the combustion gases in a carbon black manufacturing process. In another specific aspect this invention relates to method and apparatus for using off-gas to provide some combustion heat to the combustion gases in the carbon black process. In still another aspect this invention relates to method and apparatus for using off-gas to provide some combustion heat to the combustion gases in the carbon black process while holding the total volume of hot combustion gases constant at a preselected temperature.

When combusting a combustible fuel, with about a stoichiometric amount of oxygen, in a combustion tunnel before introduction of the resulting combustion gases into the carbon black combustion chamber, it has been found that the temperature of the combustion gases can exceed a temperature which will damage the refractory lining of the combustion tunnel. To prevent the temperature of the combustion gases from exceeding a temperature which will damage the refractory lining of the combustion tunnel it has been common in the past to introduce excess oxygen or air to reduce the temperature of the combustion gases. However, if excess oxygen is provided for combustion, then the excess oxygen will oxidize a portion of the carbonaceous feed and thereby reduce the yield of carbon black.

In more recently developed carbon black production systems, the off-gas from a carbon black manufacturing process is utilized to lower the temperature of the combustion gases produced from combustion of a fuel using about a stoichiometric amount of oxygen. The off-gas from a carbon black manufacturing process contains substantially no oxygen and thus very little excess oxygen is introduced into the carbon black reactor by the off-gas. The off-gas from a carbon black manufacturing process contains some hydrogen and carbon monoxide which can be used to provide some combustion heat to the combustion gases by being burned in the combustion tunnel, thus reducing the use of the more expensive high BTU fuel used in the carbon black process.

While some previous systems have utilized the off-gas from a carbon black manufacturing process to lower the temperature of the combustion gases and as a source of additional heat in the combustion chamber, the problem of using the off-gas from a carbon black manufacturing process while still maintaining a constant quality of carbon black has not been addressed. When the off-gas from a carbon black process is utilized to provide some combustion heat to the combustion chamber, additional oxygen or air must be introduced into the combustion tunnel to maintain a stoichiometric amount of oxygen in the combustion tunnel. Also shrinkage of the off-gas from the carbon black process will occur as the hydrogen and carbon monoxide are burned in the combustion tunnel. This will affect (decrease) the total volume of hot combustion gases which is provided to the carbon black reaction chamber, thus affecting the quality of the carbon black being produced if steps are not taken to maintain the total volume of the hot combustion gases constant while using the off-gas from a carbon black process to lower the temperature of the combustion gases and as a source of additional heat in the combustion chamber.

It is thus an object of this invention to provide method and apparatus for using off-gas from a carbon black process to lower the temperature of the combustion gases in the carbon black process. Another object of this invention is to provide method and apparatus for using off-gas to provide some combustion heat to the combustion gases in the carbon black process. Still another object of this invention is to provide method and apparatus for using off-gas to provide some combustion heat to the combustion gases in the carbon black process while holding the total volume of hot combustion gases substantially constant at a preselected temperature.

In accordance with the present invention, method and apparatus is provided whereby off-gas from at least one carbon black process is supplied to the combustion tunnel of the carbon black reactor. Sufficient air is introduced into the combustion tunnel to maintain a stoichiometric relationship between the fuel gas, including the off-gas, in the combustion tunnel of the carbon black reactor. The flow of off-gas to the carbon black combustion tunnel is controlled so as to maximize the use of the off-gas while still maintaining the total volume of hot combustion gases substantially constant at a preselected substantially constant temperature. This is accomplished by manipulating both the flow of the primary fuel gas and the flow of the off-gas in such a manner that the total volume of hot combustion gases produced by substantially stoichiometric combustion of the fuel gas and off-gas is constant at a preselected substantially constant temperature when shrinkage due to combustion of hydrogen and carbon monoxide in the off-gas is taken into account.

The off-gas from a carbon black filter or the cooled smoke from upstream of the filter can be utilized to quench the carbon black reaction in the carbon black reaction chamber. The flow of off-gas or cooled smoke as a quench fluid to the carbon black reaction chamber is controlled in such a manner that a desired temperature in the carbon black reaction chamber is maintained which will provide the desired carbon black product.

Figure 2:
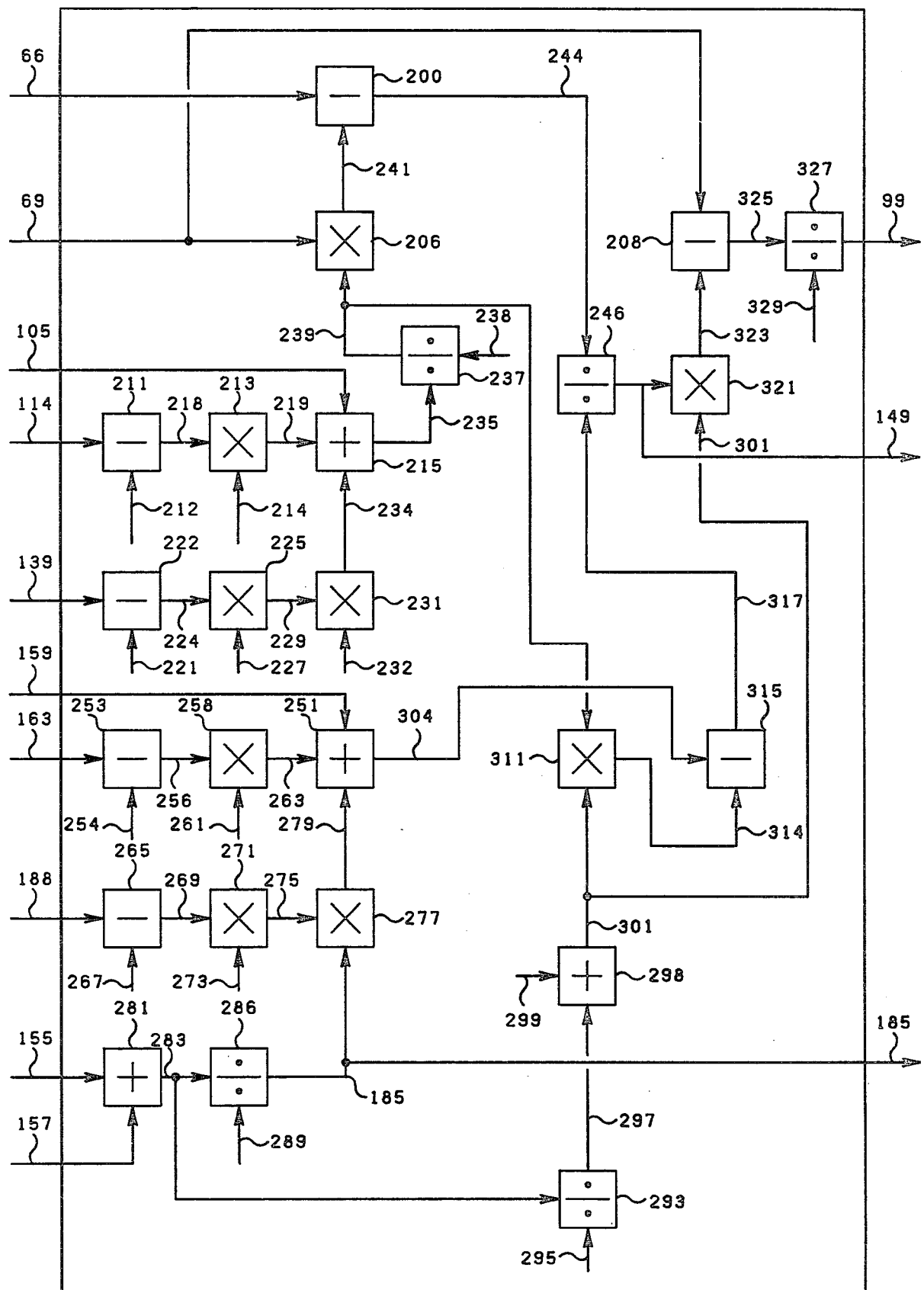

Other objects and advantages of the invention will be apparent from the detailed description of the invention and the appended claims as well as from the detailed description of the drawings in which:

FIG. 1 is a schematic representation of the apparatus used for producing carbon black in the present invention together with the associated control system for the carbon black process; and FIG. 2 is a schematic representation of the computer logic utilized to process the measured data provided to the computer to provide the set points required by the control system illustrated in FIG. 1.

For the sake of simplicity the invention is illustrated and described in terms of a single carbon black reactor having a single reaction chamber. The invention, however, is applicable to multiple carbon black reactors and is also applicable to carbon black reactors having multiple combustion chambers.

Although the invention is illustrated and described in terms of a specific carbon black reactor and a specific control configuration, the applicability of the invention described herein extends to other types of carbon black reactors and also extends to different types of control system configurations which accomplish the purpose of the invention. Lines designated as signal lines in the drawings are electrical in this preferred embodiment. However, the invention is also applicable to pneumatic, mechanical, hydraulic, or other signal means for transmitting information. In almost all control systems some combination of these types of signals will be used. However, use of any other type of signal transmission, compatible with the process and equipment in use, is within the scope of the invention.

Controllers shown may utilize the various modes of control such as proportional, proportional-integral, proportional-derivative, or proportional-integral-derivative. In this preferred embodiment proportional-integral controllers are utilized. The operation of these types of controllers is well known in the art. The output control signal of a proportional-integral controller may be represented as $$S = K_1 E + K_2 \int E Dt$$

where
S = output control signal;
E = difference between two input signals; and
$K_1$ and $K_2$ are constants.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic control elements, such as pneumatically operated valve means in conjuction with electrical analog signal handling and translation apparatus, the apparatus and method of the invention can be implemented using a variety of specific equipment available to and understood by those skilled in the process control art. Likewise the format of the various signals can be modified substantially in order to accommodate signal format requirements of the particular installation, safety factors, the physical characteristics of the measuring or control instruments and other similar factors. For example, a raw flow measurement signal produced by differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known relationship to the measured parameter. In addition, all signals could be translated into a "suppressed zero" or other similar format in order to provide a "live zero" and prevent an equipment failure from being erroneously interpreted as a "low" or "high" measurement or control signal. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or a desired process value is therefore one from which the information regarding the measured or desired value can be readily retrieved regardless of the exact mathematical relationship between the signal units and the measured or desired process units.

Referring now to the drawings and in particular to FIG. 1, a carbon black reactor 11 having a combustion tunnel 12, combustion or precombustion chamber 13, and a reaction chamber 14 is illustrated. A carbonaceous feed is supplied to the carbon black combustion chamber 13 through conduit means 16. Fuel gas and off-gas from the separation means, which is preferably a bag filter 28 is supplied to the carbon black combustion tunnel 12 through conduit means 18. The hot combustion gases produced in the carbon black combustion tunnel 12 are introduced into the carbon black combustion chamber 13 preferably in a generally tangential manner, with respect to the carbon black reaction chamber 14, so as to effect a vortex flow of the hot combustion gases along the length of the carbon black reaction chamber 14. The hot combustion gases introduced from the carbon black combustion tunnel 12 contact the carbonaceous feed at a temperature sufficiently high to pyrolyze a substantial portion of the carbonaceous feed to carbon black particles. After a predetermined length of reaction time, depending mainly on desired photelometer, the effluent flowing through the reaction chamber 14 is quenched by contact with cooled smoke from the heat exchanger 23 which is introduced into the reaction chamber 14 through conduit means 31. It is noted that other quench fluids can be used such as water. However, the use of the cooled smoke from the heat exchanger 23 is desirable in that the filter 28 is not required to handle the large amounts of water vapor which will be produced if water is used as the quench fluid.

The effluent from the carbon black reaction chamber 14, which contains the carbon black particles and other gases is supplied through conduit means 21 to the filter 28. In a preferred embodiment of the invention the heat exchanger 23 is operably connected to conduit means 21 to cool the effluent from the carbon black reaction chamber 14 before it enters the filter 28. The filter 28 is utilized to separate the carbon black particles from the gaseous portion of the effluent. The carbon black particles separated by the filter 28 are provided through conduit means 25 to a processing, such as pelleting. The separated gaseous portion, which has been referred to as off-gas in the description of the present invention, can be recycled at least in part to be used as a quench fluid for the reaction chamber 14 and can be also utilized as a quench fluid for the combustion tunnel 12 as well as providing heat to the combustion chamber 13. The off-gas can be provided through conduit means 33 to conduit means 31 and passed to conduit means 35. Any unused portion of the off-gas is vented through control valve 37 located in conduit means 33. The off-gas is provided to conduit means 18 which is operably connected to the combustion tunnel 12 through conduit means 35. Air or other oxygen containing gas required to supply a stoichiometric amount of oxygen to burn the hydrogen and carbon monoxide in the off-gas is supplied through conduit means 41. Conduit means 41 is operably connected to conduit means 18.

A high BTU fuel is provided through conduit means 43 and conduit means 18 to the combustion tunnel 12. Preferably a stoichiometric amount of oxygen required to burn the high BTU fuel is provided through conduit means 45 and conduit means 18 to the combustion tunnel 12. In this preferred embodiment of the invention, methane is utilized as the high BTU fuel but other suitable fuels can also be used in the carbon black process. Preferably air is utilized to provide the oxygen required to combust the high BTU fuel in the combustion tunnel 12.

It is common for a number of carbon black reactors to be operated in a common facility. In plants where a number of carbon black reactors are employed the off-gas from other carbon black filters can be supplied to the combustion tunnel 12 through conduit means 47 which is operably connected to conduit means 35. In like manner any off-gas or other material having combustible material flowing through control valve 37 may be supplied to a combustion tunnel of other carbon black reactors.

Control of the flow rate of the carbonaceous feed through conduit means 16 is accomplished by means of pneumatic control valve 51 located in conduit means 16. The flow rate of the carbonaceous feed through conduit means 16 is measured by flow sensor 52 which transmits a signal 53, representative of the flow rate of the carbonaceous feed in conduit means 16, to flow transducer 55. Flow transducer 55 supplies a signal 56, representative of the flow rate of the carbonaceous feed in conduit means 16, to flow controller 58 and multiplying means 64. Flow controller 58 is also supplied with a set point signal 59, representative of the desired flow rate of the carbonaceous feed through conduit means 16. Signal 60, representative of a comparison of the actual and desired flow rates of the carbonaceous feed through conduit means 16, is supplied as a control signal from flow controller 58 to pneumatic control valve 51.

Multiplying means 64 is also supplied with a signal 63, representative of the BTU/gallon required to convert the carbonaceous feed to the desired carbon black product. Signal 66, which is supplied by multiplying means 64, is thus representative of the BTU/hr. required to convert the carbonaceous feed to the desired carbon black product. Signal 66 is supplied as an input to computer means 75 and is also supplied as an input to dividing means 68. Dividing means 68 is also supplied with a signal 67, representative of the difference between the actual temperature of the hot combustion gases in the combustion tunnel 12 and a base temperature, with the difference ($\Delta T$) being multiplied by the specific heat ($C_P$) of the combustion gases. Signal 69, representative of the total volume of hot combustion gases which must be supplied to the combustion chamber 13 to maintain a desired temperature in the combustion chamber 13, is supplied from dividing means 68 as an input to computer means 75.

The flow of the off-gas through conduit means 31 to the reaction chamber 14 is controlled by means of pneumatic flow controller 81. The temperature in the reaction chamber 14 is measured and is transmitted as signal 84 by temperature transducer 83. Signal 84 is supplied from temperature transducer 83 to temperature controller 86. Temperature controller 86 is also supplied with a set point signal 87, representative of the desired temperature at the outlet end of the reaction zone 14. Signal 89 which is representative of a comparison of the actual and desired temperatures at the outlet end of the reaction chamber 14 is supplied from temperature controller 86 to pneumatic control valve 81. The pneumatic control valve 81 is manipulated in response to signal 89 to thereby control the flow rate of the off-gas through conduit means 31 to the reaction chamber 14 to thereby maintain a desired temperature at the outlet end of the reaction chamber 14 where the carbon black reaction is quenched.

The flow rate of the high BTU fuel gas through conduit means 43 is controlled by pneumatic control valve 91 which is located in conduit means 43. Flow sensor 93 senses the flow rate of the high BTU fuel gas through conduit means 43 and a signal 95, representative of the actual flow rate of the high BTU fuel gas through conduit means 43, is transmitted to flow controller 98 from flow transducer 94. Flow controller 98 is also supplied with a set point signal 99 representative of the desired flow rate of the high BTU fuel gas through conduit means 43. The desired flow rate signal 99 is calculated by computer means 75 in response to the process variables input to computer means 75. Signal 99 is supplied from computer means 75 to the flow controller 98. Signal 101, representative of a comparison of the actual and desired flow rates, is provided to pneumatic control valve 91 from flow controller 98. Pneumatic control valve 91 is manipulated in response to signal 101 to thereby maintain the flow rate of the high BTU fuel gas through conduit means 43 at a desired level. The high BTU fuel gas flowing through conduit means 43 is analyzed by analyzer transducer 104 to determine the BTU content of the fuel gas. The analyzer transducer 104 may be a chromatographic analyzer or other suitable analyzer capable of measuring the BTU content of a fuel gas. Signal 105, representative of the BTU content of the fuel gas flowing through conduit means 43, is supplied from analyzer transducer 104 as an input to computer means 75. The temperature of the high BTU fuel gas flowing through conduit means 43 is measured and is transmitted as signal 114 to computer means 75 by temperature transducer 112.

The flow of air through conduit means 45 is controlled by pneumatic control valve 121. The actual flow rate of the air flowing through conduit means 45 is measured by flow sensor 123. Signal 126, representative of the actual flow rate of the air flowing through conduit means 45, is transmitted by temperature transducer 124 to flow controller 127. Flow controller 127 is also supplied with a set point 129, representative of the flow rate of air required to provide a stoichiometric amount of oxygen for the high BTU fuel gas in the combustion tunnel 12. The set point signal 129 is calculated by supplying signal 95, representative of the actual flow rate of the fuel gas through conduit means 43, and signal 137, representative of the required ratio between the flow rate of the air through conduit means 45 and the flow rate of the high BTU fuel gas through conduit means 43, to multiplying means 133. Multiplying means 133 supplies signal 129 to flow controller 127. Temperature transducer 138 provides a signal 139, representative of the temperature of the air flowing through conduit means 45, to computer means 75.

The flow rate of the off-gas flowing through conduit means 35 is controlled by pneumatic control valve 141. Flow sensor 143 measures the actual flow rate of the off-gas flowing through conduit means 35. Signal 146, representative of the actual flow rate of the off-gas flowing through conduit means 35, is transmitted from flow transducer 144 to flow controller 148. Flow controller 148 is also supplied with a set point signal 149 which is representative of the desired flow rate of the off-gas through conduit means 35. Signal 149 is calculated by computer means 75 in response to the process variables input to the computer means 75. Signal 149 is transmitted from computer means 75 to the flow controller 148. Signal 151, representative of a comparison of the actual and desired flow rates of the off-gas through conduit means 35, is supplied from flow controller 148 to pneumatic control valve 141. Pneumatic control valve 141 is manipulated in response to signal 151 to thereby maintain the flow rate of the off-gas through conduit means 35 at a required level.

Analyzer transducer 153 is utilized to analyze the off-gas flowing through conduit means 35 and to provide three output signals to computer means 75. Signal 155 from analyzer transducer 153 is representative of the hydrogen content in the off-gas flowing through conduit means 35. Signal 157 is representative of the carbon monoxide content of the off-gas flowing through conduit means 35. Signal 159 is representative of the BTU content of the off-gas flowing through conduit means 35. The temperature of the off-gas flowing through conduit means 35 is provided as signal 163 to computer means 75 by temperature transducer 161.

The flow of air through conduit means 41 is controlled by pneumatic control valve 171. The actual flow rate of the air flowing through conduit means 41 is measured by flow sensor 173. Signal 175, representative of the actual flow rate of the air flowing through conduit means 41, is supplied by flow transducer 174 to flow controller 178. Flow controller 178 is also supplied with a set point signal 177, representative of the required flow rate of air necessary to supply a stoichiometric volume of oxygen for the off-gas flowing through conduit means 35. Signal 177 is calculated by multiplying means 183. Signal 146, representative of the actual flow rate of off-gas through conduit means 35 is supplied to multiplying means 183. Multiplying means 183 is also supplied with a signal 185, representative of the required ratio of air to off-gas. Signal 185 is calculated by computer means 75 in response to the process variables input to computer means 75. Signal 146 is multiplied by signal 185 to provide signal 177. Signal 179, which is representative of a comparison of the actual and desired flow rates of the air through conduit means 41, is supplied as the control signal to pneumatic control valve 171. Pneumatic control valve 171 is manipulated in response to signal 179 to thereby maintain the flow rate of the air through conduit means 41 at a desired level. Temperature transducer 187 provides a signal 189, representative of the temperature of the air flowing through conduit means 41, to computer means 75.

A number of electronic and/or pneumatic systems can be used to automatically calculate the set point signals 99, 149, and 185 which are provided by computer means 75 in the preferred embodiment of the invention illustrated in FIG. 1. The set point signals 99, 149 and 185 could also be calculated by hand if desired. FIG. 2 illustrates, in analog form, the computer logic required to calculate the set point signals 99, 149 and 185.

The following development of the set points 99, 149 and 185, utilized in the present invention, is provided to clarify the analog development illustrated in FIG. 2. The volume of off-gas required may be determined by $$V_{OG} = \frac{H_T - (V_T)(H_{FG})}{H_{OG} - (B_{OG})(H_{FG})} \quad (1)$$

where
$V_{OG}$ = total volume of off-gas required (SCF/HR);
$H_T$ = total heat required (BTU/HR);
$V_T$ = total volume of hot combustion gases required (SCF/HR);
$H_{FG}$ = heat added by burning one standard cubic foot (SCF) of fuel gas stoichiometrically with air plus the sensible heat of the fuel gas and air determined at a base temperature of 60° F. divided by the SCF produced by the burning of the 1 SCF of fuel gas in a stoichiometric amount of air;
$H_{OG}$ = heat added by burning one SCF of off-gas stoichiometrically with air plus the sensible heat of the off-gas and air determined at a base temperature of 60° F.; and
$B_{OG}$ = the SCF of off-gas burned with air stoichiometrically to produce one SCF of hot combustion gases.

The value of $H_{FG}$ in equation (1) may be determined by $$H_{FG} = \frac{H_{CFG} + (T_{FG} - 60)(C_{PFG}) + R_1(T_{AFG} - 60)(C_{PAFG})}{V_{HG}} \quad (2)$$

where
$H_{CFG}$ = heat of combustion of fuel gas, (BTU/SCF);
$T_{FG}$ = temperature of fuel gas, (°F.);
$C_{PFG}$ = specific heat of fuel gas, at $T_{FG}$, (BTU/SCF/°F.);
$R_1$ = volume ratio of air to fuel gas, (stoichiometric combustion);
$T_{AFG}$ = temperature of air supplied for fuel gas, (°F.);
$C_{PAFG}$ = specific heat of air at $T_{AFG}$ supplied for fuel gas (BTU/SCF/°F.);
and
$V_{HG}$ = SCF produced by the burning one SCF of fuel gas in a stoichiometric amount of air.

The value of $H_{OG}$ in equation (1) may be determined by $$H_{OG} = H_{COG} + (T_{OG} - 60)(C_{POG}) + R_2(T_{AOG} - 60)(C_{PAOG}) \quad (3)$$

where
$H_{COG}$ = heat of combustion of off-gas, (BTU/SCF);
$T_{OG}$ = temperature of off-gas, (°F.);
$C_{POG}$ = specific heat of off-gas at $T_{OG}$ (BTU/SCF/°F.);
$R_2$ = volume ratio of air to off-gas (Stoichiometric combustion);
$T_{AOG}$ = temperature of air supplied for off-gas, (°F.);
$C_{PAOG}$ = specific heat of air supplied for off-gas, at $T_{AOG}$ (BTU/SCF/°F.).

The value of $B_{OG}$ in equation 1 may be determined by $$B_{OG} = 1 + S \quad (4)$$

where
S = shrinkage in SCF per SCF of off-gas stoichiometrically combined with air.

The value of $R_2$ in equation 3 may be determined by $$R_2 = \frac{Y + Z}{40} \quad (5)$$

where
Y = volume percent CO in off-gas; and
Z = volume percent $H_2$ in off-gas.

The value of S in equation 4 may be determined by $$S = \frac{Y+Z}{50} \quad (6)$$

where

Y and Z are as previously defined.

The volume of high BTU fuel gas required may be determined by $$V_{FG} = \frac{V_T - (V_{OG})(B_{OG})}{V_{HG}} \quad (7)$$

where $V_T$, $V_{OG}$, S, and $V_{HG}$ are as previously defined.

The set point 185 provided to multiplying means 183 is equal to $R_2$ as defined above and may be calculated by use of equation (5).

The symbols defined in the preceding paragraphs are used in the description of FIG. 2. Referring now to FIG. 2, signal 66 which is representative of $H_T$ is supplied as one input to subtracting means 200. Signal 69, which is representative of $V_T$, is supplied as one input to multiplying means 206 and subtracting means 208. Signal 105, which is representative of $H_{CFG}$, is supplied as one input to summing means 215. Signal 114, which is representative of $T_{FG}$, is supplied as one input to subtracting means 211. Subtracting means 211 is also supplied with signal 212, which is representative of the base temperature (60° F.) for the computer calculations. Signal 218, which is representative of ($T_{FG}$−60) is supplied as one input to multiplying means 213. Multiplying means 213 is also supplied with signal 214, which is representative of $C_{PFG}$. Signal 219, which is representative of ($T_{FG}$−60) ($C_{PFG}$), is supplied from multiplying means 213 as a second input to summing means 215. Signal 139, which is representative of $T_{AFG}$, is supplied as one input to subtracting means 222. Subtracting means 222 is also supplied with signal 221, which is representative of the base temperature (60° F.) for the computer calculations. Signal 224, which is representative of ($T_{AFG}$−60), is supplied as one input from subtracting means 222 to multiplying means 225. Multiplying means 225 is also supplied with signal 227, which is representative of $R_1$. Signal 229, which is representative of ($R_1$) ($T_{AFG}$−60), is supplied as one input to multiplying means 231 from multiplying means 225. Multiplying means 231 is also supplied with signal 232, which is representative of $C_{PAFG}$. Signal 234, which is representative of $R_1$ ($T_{AFG}$−60) ($C_{PAFG}$), is supplied as a third input to summing means 215 from multiplying means 231. Signal 235, which is representative of $H_{CFG}+(T_{FG}-60)(C_{PFG})+R_1(T_{AFG}-60)(C_{PAFG})$, is supplied as one input to dividing means 237. Dividing means 237 is also supplied with signal 238, which is representative of $V_{HG}$. Signal 239, which is representative of $H_{FG}$, is supplied as a second input to multiplying means 206. Signal 241, which is representative of ($V_T$) ($H_{FG}$), is supplied as a second input to subtracting means 200. Signal 244, which is representative of $H_T-(V_T)(H_{FG})$, is supplied as one input to dividing means 246.

Signal 159, which is representative of $H_{COG}$, is supplied as one input to summing means 251. Signal 163, which is representative of $T_{OG}$, is supplied as one input to subtracting means 253. Subtracting means 253 is also provided with a signal 254, which is representative of the base temperature (60° F.) for the computer calculations. Signal 256, which is representative of ($T_{OG}$−60), is supplied as an input to multiplying means 258 from subtracting means 253. Multiplying means 258 is also supplied with signal 261, which is representative of $C_{POG}$. Signal 263, which is representative of ($T_{OG}$−60) ($C_{POG}$), is supplied as a second input to summing mean 251 from multiplying means 258. Signal 188, which is representative of $T_{AOG}$, is supplied as one input to subtracting means 265. Subtracting means 265 is also supplied with a signal 267, representative of the base temperature (60° F.) for the computer calculations. Signal 269, which is representative of ($T_{AOG}$-60), is supplied as one input to multiplying means 271. Multiplying means 271 is also supplied with signal 273, which is representative of $C_{POAG}$. Signal 275, which is representative of ($T_{AOG}$−60) ($C_{PAOG}$), is supplied as one input to multiplying means 277 from multiplying means 271. Signal 155, which is representative of Y, is supplied as one input to summing means 281. Signal 157, which is representative of Z, is supplied as a second input to summing means 281. Signal 283, which is representative of Y+Z, is supplied to dividing means 286 and to dividing means 293. Dividing means 286 is also supplied with a signal 289, representative of a constant 40. Signal 185, which is representative of (Y+Z)/40, is supplied as a second input to multiplying means 277 and is also supplied as a set point to multiplying means 183 illustrated in FIG. 1. Signal 185 was defined as $R_2$ in the equations which were previously developed.

Signal 279, which is representative of $R_2$ ($T_{AOG}$−60) ($C_{PAOG}$), is supplied as a third input to summing means 251 from multiplying means 277. Signal 304, which is representative of $H_{OG}$, is supplied as one input to subtracting means 315.

Dividing means 293 is also supplied with a signal 295, representative of the constant 50. Signal 297, representative of (Y+Z)/50, is supplied as one input to summing means 298. Summing means 298 is also supplied with a signal 299, representative of the constant +1. Signal 301, which is representative of $B_{OG}$, is supplied as an input to multiplying means 311 from summing means 298. Signal 239, which is representative of $H_{FG}$, is also supplied to multiplying means 311. Signal 314, which is representative of ($B_{OG}$) ($H_{FG}$), is supplied as a second input to subtracting means 315. Signal 317, which is representative of $H_{OG}-(B_{OG})(H_{FG})$, is supplied as a second input to dividing means 246. Signal 149 which is representative of $V_{OG}$ is supplied from dividing means 246 as a set point to flow controller 148. Signal 149 is also supplied to multiplying means 321. Multiplying means 321 is also supplied with signal 301, which is representative of $B_{OG}$. Signal 323, which is representative of ($V_{OG}$) ($B_{OG}$), is supplied as a second input to subtracting means 208. Signal 325, which is representative of $V_T-(V_{OG})(B_{OG})$, is supplied as one input to dividing means 327 from subtracting means 208. Dividing means 327 is also supplied with signal 329, which is representative of $V_{HG}$. Signal 99, which is representative of $V_{FG}$, is supplied as a set point to flow controller 98 illustrated in FIG. 1.

In the practice of the present invention the flow of air through conduit means 45 and 41 is controlled so as to provide a stoichiometric amount of oxygen in the combustion chamber 12. To produce certain types of carbon black, it is desirable to have excess oxygen so that partial oxidation of the make-hydrocarbon results. If excess oxygen is desired it is simply necessary to modify the set point signal 137 supplied to multiplier 133 to provide a higher amount of oxygen to the combustion chamber 12.

The temperature of the hot combustion gases in the combustion tunnel 12 is held below a temperature which would damage portions of the carbon black reactor 11 but the temperature is still sufficiently high to achieve pyrolysis of the carbonaceous feed. Refractory damaging temperature is the temperature at which softening of the refractory lining occurs or the temperature at which spalling can be caused. For example, if the refractory is 90 percent alumina, the temperature of the hot combustion gases should be held below about 3100° F. for continuous operation. If the refractory is chrome alumina, then the hot combustion gas temperature should be held below about 3500° F. for continuous operation.

The temperature of the air entering through conduit means 45 and conduit means 41 will be dependent upon the particular process used and generally will be between about 100° F. and about 1200° F. The temperature of the high BTU fuel gas which is supplied through conduit means 43 will preferably be between 100° F. and 700° F. The temperature of the off-gas flowing through conduit means 35 will preferably be below about 700° F. and will preferably have an oxygen content of less than about 0.5 percent by volume. This off-gas is preferably then preheated after leaving the filter, e.g. from about 400° F. up to the higher temperature.

The following "calculated" examples are provided to illustrate possible modes of operation of a carbon black system incorporating the present invention. Methane is used as the high BTU fuel gas in the calculated examples. The methane, air and off-gas are all preheated to 660° F.

EXAMPLE I

| | |
|---|---|
| Make-hydrocarbon feed rate | 250 gal/hr. |
| BTU/GAL of oil required | 41,800 BTU/GAL. |
| Total BTU/HR in hot gases ($H_T$) | 10,450,000 BTU/HR |
| Total hot gases ($V_T$) | 128,000 SCF/HR |
| Required temperature in combustion tunnel 12 | 3200° F. |
| Volume percent CO in off-gas (Y) | 10% |
| Volume percent $H_2$ in off-gas (Z) | 10% |
| Heat of combustion of off-gas $H_{COG}$ | 60 BTU |
| Heat of combustion of fuel gas ($H_{CFG}$) | 1000 BTU |
| Air to fuel-gas ratio ($R_1$) | 10:1 |
| Air to off-gas ratio ($R_2$) | 0.5:1 |
| Required volume of off-gas ($V_{OG}$) | 48,443 SCF/HR |
| Required volume of air for off-gas | 24,222 SCF/HR |
| Required volume of methane | 5,471 SCF/HR |
| Required volume of air for methane | 54,710 SCF/HR |
| Volume of hot combustion gases contributed by off-gas | 67,821 SCF/HR |
| Volume of hot combustion gases contributed by methane | 60,181 SCF/HR |
| Total volume of hot combustion gases | 128,002 SCF/HR |

EXAMPLE II

| | |
|---|---|
| Make-hydrocarbon feed rate | 250 gal/hr. |
| BTU/GAL of oil required | 41,800 BTU/GAL. |
| Total BTU/HR in hot gases ($H_T$) | 10,450,000 BTU/HR |
| Total hot gases ($V_T$) | 128,000 SCF/HR |
| Required temperature in combustion tunnel 12 | 3200° F. |
| Volume percent CO in off-gas (Y) | 12% |
| Volume percent $H_2$ in off-gas (Z) | 12% |

-continued

| | |
|---|---|
| Heat of combustion of off-gas ($H_{COG}$) | 72 BTU |
| Heat of combustion of fuel gas ($H_{CFG}$) | 1000 BTU |
| Air to fuel-gas ratio ($R_1$) | 10:1 |
| Air to off-gas ratio ($R_2$) | 0.6:1 |
| Required volume of off-gas ($V_{OG}$) | 52,467 SCF/HR |
| Required volume of air for off-gas | 31,480 SCF/HR |
| Required volume of methane | 4,577 SCF/HR |
| Required volume of air for methane | 45,770 SCF/HR |
| Volume of hot combustion gases contributed by off-gas | 77,651 SCF/HR |
| Volume of hot combustion gases contributed by methane | 50,347 SCF/HR |
| Total volume of hot combustion gases | 127,998 SCF/HR |

As the volume percent of CO and $H_2$ in the off-gas changes the amount of shrinkage of the off-gas in the combustion tunnel 12 also changes. However, as is illustrated in Examples I and II, even though the volume percent of CO and $H_2$ in the off-gas and thus the heat of combustion of the off-gas changes, the control system of the present invention is capable of maintaining a substantially constant temperature and a substantially constant volume of hot combustion gases in the combustion chamber 13. Maintaining a constant temperature and a constant volume of hot combustion gases in a major factor in producing carbon black of a constant quality.

The invention has been described in terms of a preferred embodiment as is illustrated in FIGS. 1 and 2. Specific components which can be used in the practice of the invention as illustrated in FIGS. 1 and 2 such as controllers 58, 86, 98, 127, 148 and 178; flow sensors 52, 93, 123, 143 and 173; and associated flow transducers 55, 94, 124, 144 and 174; temperature transducers 83, 112, 138, 161, and 187; control valves 51, 81, 91, 121, 141, and 171 are each well known commercially available control components such as are described at length in Perry's Chemical Engineers' Handbook, 4th Edition, Chapter 22, McGraw-Hill.

Analyzer transducers 104 and 153 are in this preferred embodiment chromatographic analyzers. A suitable chromatographic analyzer is the Optichrom2100 manufactured by Applied Automation, Bartlesville, Oklahoma. The multiplying means 64, 133, and 183 and the dividing means 68 illustrated in FIG. 1 as well as the summing, subtracting, multiplying and dividing means illustrated in FIG. 2 are in this preferred embodiment the number B05885 Multiuse Amp manufactured by Applied Automation, Bartlesville, Oklahoma.

Also, for reasons of brevity and clarity, conventional auxiliary equipment such as pumps for feed and fuel gases, additional heat exchangers, additional measurement-control devices, and additional processing equipment required in carbon black production have not been included in the above description as they play no part in the explanation of the invention.

While the invention has been described in terms of the presently preferred embodiment, reasonable variations and modifications are possible, by those skilled in the art, within the scope of the described invention and the appended claims. For example, the type of carbon black being produced may require that the air to fuel gas ratio be held at a higher ratio than that necessary to provide a stoichiometric amount of oxygen in the combustion tunnel 12. Also the basic control method illustrated in FIGS. 1 and 2 may frequently be used as a subsystem for a more comprehensive carbon black process control.

That which is claimed is:

1. In an apparatus for producing carbon black comprising:

a carbon black reactor having a reaction chamber, a combustion chamber, and a combustion tunnel, said combustion tunnel opening into said combustion chamber for introducing hot combustion gases into said combustion chamber, said combustion chamber opening into the carbon black reaction chamber for introducing hot combustion gases and a carbonaceous feed into said carbon black reaction chamber;

means for supplying a carbonaceous feed to said combustion chamber, the contacting of said carbonaceous feed with said hot combustion gases in said combustion chamber and said carbon black reaction chamber converting said carbonaceous feed to carbon black and gas;

means for separating said carbon black from said gas;

means for supplying said carbon black and said gas from said carbon black reaction chamber to said means for separating said carbon black from said gas;

means for supplying at least a portion of the gas which has been separated from said carbon black from said means for separating said carbon black from said gas to said combustion tunnel as a recycle gas;

means for supplying fuel to said combustion tunnel; and means for supplying an oxygen containing gas to said combustion tunnel, the combustion of said recycle gas and said fuel with said oxygen containing gas supplying said hot combustion gases;

the improvement comprising:

means for controlling the flow rate of said fuel to said combustion tunnel;

means for controlling the flow rate of said recycle gas to said combustion tunnel; and means for controlling the flow rate of said oxygen containing gas to said combustion tunnel so as to maintain a desired ratio of said oxygen containing gas to said fuel and a desired ratio of said oxygen containing gas to said recycle gas, the rate of flow of said fuel and the rate of flow of said recycle gas to said combustion tunnel being controlled so as to maintain the ratio of the volume of said hot combustion gases introduced into said combustion chamber to the volume of said carbonaceous feed introduced into said combustion chamber substantially constant at a desired temperature for said hot combustion gases introduced into said combustion chamber.

2. Apparatus in accordance with claim 1 wherein said means for controlling the rate of flow of said fuel to said combustion tunnel comprises:

means for establishing a first signal representative of the actual flow rate of said fuel;

means for establishing a second signal representative of the desired flow rate of said fuel;

means for comparing said first signal and said second signal and for establishing a third signal reponsive to the difference between said first signal and said second signal; and means for controlling the actual flow rate of said fuel in response to said third signal.

3. Apparatus in accordance with claim 2 wherein said means for controlling the rate of flow of said recycle gas to said combustion tunnel comprises:

means for establishing a fourth signal representative of the actual flow rate of said recycle gas;

means for establishing a fifth signal representative of the desired flow rate of said recycle gas;

means for comparing said fourth signal and said fifth signal and for establishing a sixth signal reponsive to the difference between said fourth signal and said fifth signal; and means for controlling the flow rate of said recycle gas in response to said sixth signal.

4. Apparatus in accordance with claim 3 wherein said means for supplying an oxygen containing gas to said tunnel chamber comprises:

means for supplying a first flow of said oxygen containing gas to said tunnel chamber to maintain a desired ratio of said oxygen containing gas to said fuel; and means for supplying a second flow of said oxygen containing gas to said tunnel chamber to maintain a desired ratio of said oxygen containing gas to said recycle gas.

5. Apparatus in accordance with claim 4 wherein said means for controlling the rate of flow of said oxygen containing gas to said combustion tunnel comprises:

means for establishing a seventh signal representative of the actual flow rate of said first flow of said oxygen containing gas;

means for establishing an eighth signal representative of the desired flow rate of said first flow of said oxygen containing gas;

means for comparing said seventh signal and said eighth signal and for establishing a ninth signal responsive to the difference between said seventh signal and said eighth signal;

means for controlling the flow rate of said first flow of said oxygen containing gas in response to said ninth signal;

means for establishing a tenth signal representative of the actual flow rate of said second flow of said oxygen containing gas;

means for establishing an eleventh signal representative of the desired flow rate of said second flow of said oxygen containing gas;

means for comparing said tenth signal and said eleventh signal and for establishing a twelfth signal responsive to the difference between said tenth signal and said eleventh signal; and means for controlling the flow rate of said second flow of said oxygen containing gas in response to said twelfth signal.

6. Apparatus in accordance with claim 5 wherein said oxygen containing gas is air, the desired ratio of said oxygen containing gas to said fuel is a stoichiometric ratio, and the desired ratio of said oxygen containing gas to said recycle gas is a stoichiometric ratio.

7. Apparatus in accordance with claim 6 wherein said means for establishing said fifth signal comprises:

means for establishing a thirteenth signal ($H_T$) representative of the total heat required of said hot combustion gases;

means for establishing a fourteenth signal ($V_T$) representative of the total volume of said hot combustion gases required;

means for establishing a fifteenth signal ($H_{FG}$) representative of the heat added by burning one standard cubic foot of said fuel stoichiometrically with said air plus the sensible heat of said fuel and said air determined at a base temperature of 60° F. divided by the standard cubic feet produced by the burning of the said fuel in a stoichiometric amount of said air;

means for multiplying said fourteenth signal and said fifteenth signal to establish a sixteenth signal representative of $(V_T)(H_{FG})$;

means for subtracting said sixteenth signal from said thirteenth signal to establish a seventeenth signal representative of $H_T-(V_T)(H_{FG})$;

means for establishing an eighteenth signal representative of the heat added by burning one standard cubic foot of said recycle gas stoichiometrically with said air plus the sensible heat of said recycle gas and said air determined at a base temperature of 60° F.;

means for establishing a nineteenth signal representative of the standard cubic feet of said recycle gas burned with said air stoichiometrically to produce one standard cubic foot of hot combustion gases;

means for multiplying said fifteenth signal and said nineteenth signal to produce a twentieth signal representative of $(B_{OG})(H_{FG})$;

means for subtracting said twentieth signal from said eighteenth signal to produce a twenty-first signal representative of $H_{OG}-(B_{OG})(H_{FG})$; and means for dividing said seventeenth signal by said twenty-first signal to establish said fifth signal.

8. Apparatus in accordance with claim 7 wherein said means for establishing said second signal comprises:

means for multiplying said nineteenth signal by said fifth signal and for establishing a twenty-second signal representative of $(V_{OG})(B_{OG})$;

means for subtracting said twenty-second signal from said fourteenth signal to establish a twenty-third signal representative of $V_T-(V_{OG})(B_{OG})$;

means for establishing a twenty-fourth signal $(V_{HG})$ representative of the standard cubic feet produced by the burning of said fuel in a stoichiometric amount of air; and means for dividing said twenty-third signal by said twenty-fourth signal to produce said second signal.

9. Apparatus in accordance with claim 8 wherein said means for establishing said eighth signal comprises:

means for establishing a twenty-fifth signal representative of the desired ratio of said air to said fuel; and means for multiplying said first signal by said twenty-fifth signal to produce said eighth signal.

10. Apparatus in accordance with claim 9 wherein said means for establishing said eleventh signal comprises:

means for establishing a twenty-sixth signal representative of the desired ratio of said air to said recycle gas; and means for multiplying said twenty-sixth signal by said fourth signal to produce said eleventh signal.

11. Apparatus in accordance with claim 1 additionally comprising:

means for supplying at least a portion of the gas which has been separated from said carbon black from said means for separating said carbon black from said gas to said carbon black reaction chamber as a quench fluid; and means for controlling the rate of flow of said quench fluid to said carbon black reaction chamber so as to maintain a desired quench temperature in said carbon black reaction chamber.

12. Apparatus in accordance with claim 11 wherein said means for controlling the flow rate of said quench fluid to said carbon black reaction chamber comprises:

means for establishing a first signal representative of the actual quench temperature in said carbon black reaction chamber;

means for establishing a second signal representative of the desired quench temperature in said carbon black reaction chamber;

means for comparing said first signal and said second signal and for establishing a third signal responsive to the difference between said first signal and said second signal; and means for controlling the flow rate of said quench fluid to said carbon black reaction chamber in response to said third signal.

* * * * *

UNITED STATES PATENT AND TRADEMARK OFFICE
CERTIFICATE OF CORRECTION

PATENT NO. : 4,237,092

DATED : December 2, 1980

INVENTOR(S) : Robert J. Lewis

It is certified that error appears in the above-identified patent and that said Letters Patent are hereby corrected as shown below:

Column 14, claim 4, line 16, before "tunnel", insert --- combustion ---
after "tunnel", delete "chamber.

line 18, before "tunnel", insert --- combustion ---
after "tunnel", delete "chamber".

line 22, before "tunnel", insert --- combustion ---
after "tunnel", delete "chamber.

Signed and Sealed this

Twenty-first Day of July 1981

[SEAL]

Attest:

Attesting Officer

GERALD J. MOSSINGHOFF

Commissioner of Patents and Trademarks